United States Patent [19]

Armstrong

[11] 4,086,332

[45] * Apr. 25, 1978

[54] DOXYCYCLINE COMPOSITIONS

[75] Inventor: William W. Armstrong, Mill Neck, N.Y.

[73] Assignee: Pfizer Inc., New York, N.Y.

[ * ] Notice: The portion of the term of this patent subsequent to Apr. 19, 1994, has been disclaimed.

[21] Appl. No.: 748,600

[22] Filed: Dec. 7, 1976

Related U.S. Application Data

[63] Continuation-in-part of Ser. No. 646,295, Jan. 2, 1976, Pat. No. 4,018,889.

[51] Int. Cl.$^2$ .................. A61K 31/79; A61K 31/65
[52] U.S. Cl. ...................................... 424/80; 424/227
[58] Field of Search ............................... 424/227, 80

[56] References Cited

U.S. PATENT DOCUMENTS

| | | | |
|---|---|---|---|
| 2,987,437 | 6/1961 | Hessel | 424/227 |
| 3,062,717 | 11/1962 | Hammer | 424/227 |
| 3,674,859 | 7/1972 | Beutel et al. | 424/227 |
| 3,932,653 | 1/1976 | Stoughton | 424/285 |
| 3,957,980 | 5/1976 | Noseworthy | 424/227 |
| 3,957,994 | 5/1976 | Schroer | 424/253 |
| 3,969,516 | 7/1976 | Stoughton | 424/181 |

FOREIGN PATENT DOCUMENTS

| | | |
|---|---|---|
| 2,313,080 | 3/1976 | France. |
| 1,053,736 | 3/1959 | Germany. |
| 2,615,140 | 10/1976 | Germany. |
| 2,557,431 | 6/1976 | Germany. |
| 1,091,287 | 4/1961 | Germany. |
| 802,111 | 9/1956 | United Kingdom. |
| 805,026 | 2/1957 | United Kingdom. |

OTHER PUBLICATIONS

Japanese Pat. Appln. Pub. No. Sho 47-303 (Jan. 6, 1972).
Japanese Pat. Appln. Pub. No. Sho 43-1758 (Jan. 22, 1968).
Gans & Higuchi–J. Pharm. Sci. vol. 46 (1957) p. 458.

*Primary Examiner*—Sam Rosen
*Attorney, Agent, or Firm*—Francis X. Murphy; Charles J. Knuth; Allen J. Spiegel

[57] ABSTRACT

Aqueous solutions of doxycycline or salts thereof, a pharmaceutically acceptable soluble magnesium compound and 2-pyrrolidone as a co-solvent, said solution having a pH of 3 to 7.5 and being useful as an injectable composition combining low viscosity, high potency, good clarity and good stability.

8 Claims, No Drawings

DOXYCYCLINE COMPOSITIONS

CROSS REFERENCE TO RELATED APPLICATION

This application is a continuation-in-part of my co-pending application Ser. No. 646,295, filed Jan. 2, 1976, now U.S. Pat. No. 4,018,889.

BACKGROUND OF THE INVENTION

This invention relates to antibiotic compositions suitable for pharmaceutical use. More particularly, it relates to aqueous doxycycline solutions containing 2-pyrrolidone.

Previous effects made to prepare high concentration doxycycline solutions have been unsuccessful. This is of particular importance in the case of veterinary parenteral compositions for administration to large animals.

Japanese Patent Publication No. Sho 47-303 discloses stable aqueous solutions of p-biphenylmethyl (dl-tropyl-α-tropinium) bromide, 2.5%, in which 2-pyrrolidone is present in a concentration of 20%. The use of polyvinylpyrrolidone at a concentration of 30% is also disclosed. The pH of these solutions is less than 7, the preferred range being 3-4.

Japanese Patent Publication No. Sho 43-1758 discloses insecticidal solutions containing hexachlorcyclohexane in alcohol and 2-pyrrolidone as solvents. The use of N-methyl pyrrolidone as a co-solvent is also disclosed.

British Patent Specification No. 802,111 discloses pesticidal compositions containing 2-pyrrolidone or N-methyl pyrrolidone as solvents for DDT, dieldrin, aldrin and similar insecticides. The use of 67-82% of 2-pyrrolidone is exemplified.

British Patent Specification No. 805,026 discloses the use of N-methyl pyrrolidone in concentrations of 40% as a solvent for various medicaments intended for parenteral administration, such as chloramphenicol, N,N'-dibenzyl ethylenediamine-dipenicillin G and procaine penicillin.

U.S. Pat. No. 2,987,437 discloses nematocidal compositions of 3,4-dichlorotetrahydrothiophene, 1,1-dioxide in 2-pyrrolidone.

German Pat. No. 1,091,287 discloses stable aqueous solutions of tyrothricin 0.25% or subtilin 0.2% for nasal or otic use prepared with the aid or pyrrolidone and/or polyvinylpyrrolidone as solubilizers. Pyrrolidone is used in a concentration of 0.5% and polyvinylpyrrolidone can be used up to 10%.

U.S. Pat. No. 3,957,980 discloses aqueous injectable solutions of doxycycline comprising a solution in water of from about 1 to 10% by weight of doxycycline, together with about 3 to 8 molar proportions of a phosphate salt selected from phosphoric acid, sodium or potassium orthophosphate, metaphosphate, pyrophosphate, tripolyphosphate or hexametaphosphate, and about 3 to eight molar proportions of a pharmaceutically acceptable magnesium salt soluble in said aqueous pharmaceutical composition, said composition having a pH value in the range of from about 1 to 3.5.

U.S. Pat. No. 3,674,859 discloses aqueous solutions of doxycycline containing from about 1 to 15% doxycycline and from about 5 percent to 40 percent by weight of polyvinylpyrrolidone having an average molecular weight that is in the range of from about 10,000 to about 60,000, said composition having a pH value in the range of from about 5 to about 8.

J. Pharm. Sci. 46, p. 458 (1957) discloses that oxytetracycline forms soluble complexes with N-methyl pyrrolidone in aqueous solution. The degree of interaction is limited by pH and solubility considerations.

SUMMARY OF THE INVENTION

It has now been found that stable high potency solutions of doxycycline can be provided by means of a novel pharmaceutical composition comprising an aqueous solution of from about 1 to 25% by weight of an antibiotic compound selected from the group consisting of doxycycline and the pharmaceutically acceptable acid addition salts thereof, about 1.8 to 2.2 molar proportions of a pharmaceutically acceptable magnesium compound soluble in said solution, and from about 10 to 70% by weight of 2-pyrrolidone, said composition having a pH value in the range of from about 3 to 7.5.

DETAILED DESCRIPTION OF THE INVENTION

Doxycycline, the therapeutically active component of this invention, is a widely used tetracycline-type antibiotic of high potency and having a superior half-life. It is particularly described in U.S. Pat. No. 3,200,149 under the chemical name α-6-deoxy-5-oxytetracycline. An effective concentration range for doxycycline in the solutions of this invention is generally from about 1 to 25% by weight of the total in the form of the free base or a pharmaceutically acceptable acid addition salt. The preferred form is the free base with the preferred concentration being from about 5% to 20% by weight, with the especially preferred concentration being from about 10% to 20% by weight.

Examples of suitable doxycycline acid addition salts which can be used include such pharmaceutically acceptable acid addition salts as hydrochloride, hydrobromide and sulfate. However, the preferred acid addition salt is doxycycline hydrochloride, e.g., in the form of doxycycline hyclate, which is doxycycline hydrochloride hemiethanolate hemihydrate.

Magnesium ions combine with doxycycline in solution to form magnesium-doxycycline chelates. Magnesium oxide is a convenient and preferred source of magnesium ions, but other magnesium compounds useful for the purpose of this invention include magnesium chloride, magnesium acetate and magnesium sulfate. The molar ratio of magnesium to doxycycline in these compositions is about from 1.8 to 2.2. This ratio is advisable to produce clear stable solutions.

2-Pyrrolidone is present as a co-solvent in a concentration of from about 10 to 70% and preferably from about 30 to 50%, based on the total weight of the composition. 2-Pyrrolidone is also known as 2-pyrrolidinone, 2-oxopyrrolidine, α-pyrrolidone and 2-ketopyrrolidine. It has an oral $LD_{50}$ of 8 gm/kg in rats and 3.8 gm/kg by intraperitoneal injection in mice. Its use allows for minimum volume per dose and satisfactory syringeability due to low viscosity of the resultant composition.

As an optional ingredient polyvinylpyrrolidone may also be present in a concentration of from about 1 to 7% by weight. The polyvinylpyrrolidone preferred for this invention is one having an average molecular weight of between about 5,000 and 100,000 (K-12 to 30) and especially between about 10,000 and 17,000 (K-17). It is present in part as a cosolubilizer and may improve tissue toleration.

The stability of these solutions for therapeutic administration is still further enhanced by the use of antioxidants such as sodium or magnesium formaldehyde sulfoxylate and monothioglycerol at levels of from about 0.01 to 1.0% by weight.

The pH value is adjusted if necessary to pH 3 to 7.5. The preferred range is pH 5 to 7. The pH can be adjusted by means of an acid that is pharmaceutically acceptable, such as hydrochloric acid or by means of an organic base, such as monoethanolamine.

The compositions of this invention are readily prepared by mixing the magnesium compound with the 2-pyrrolidone and water at about 50° C and slowly adding the doxycycline antibiotic with stirring and adjusting the pH to the desired range. If polyvinylpyrrolidone is to be included it is added to the 2-pyrrolidone and water before the addition of the magnesium compound as previously described.

These compositions are also easy to syringe over a wide temperature range and are satisfactory from a physical and chemical stability standpoint.

The use of these high potency doxycycline compositions enables a reduction of the number of injections that must be administered to large animals, such as steers, in order to receive an effective dose.

The primary application is as a parenteral composition but the new compositions can also be used for topical or oral application.

EXAMPLE 1

The following solution containing 100 mg/ml of doxycycline activity was prepared.

| | gm/100 ml |
|---|---|
| Doxycycline (based on a potency of 930 γ/mg. plus a 5% overage) | 11.29 |
| Magnesium oxide | 1.921 |
| 2-Pyrrolidone | 50.00 |
| Sodium formaldehyde sulfoxylate | 1.00 |
| Concentrated hydrochloric acid, to adjust pH to 7.3 | |
| Water q.s. to | 100 ml |

The 2-pyrrolidone was mixed with water. The solution was heated to about 50° C and the sodium formaldehyde sulfoxylate was added and dissolved with stirring. The magnesium oxide was then slurried with the solution. The doxycycline was slowly added with stirring and the pH adjusted with concentrated hydrochloric acid. The resultant solution was allowed to cool to room temperature and the pH further adjusted to 7.3 with concentrated hydrochloric acid. The solution was then brought up to volume with water.

Solutions comparable to the above were also made by adjusting the pH to 5.0 and 6.5 respectively.

EXAMPLE 2

The following solution containing 100 mg/ml of doxycycline activity was prepared using the procedure described in Example 1.

| | gm/100 ml |
|---|---|
| Doxycycline (based on a potency of 930 γ/mg plus a 5% overage) | 11.29 |
| Magnesium oxide | 1.921 |
| 2-Pyrrolidone | 40.00 |
| Sodium formaldehyde sulfoxylate | 1.00 |
| Concentrated hydrochloric acid, adjust to pH 7.2 | |
| Water q.s. to | 100 ml |

A solution comparable to the above was also made by adjusting the pH to 5.2.

EXAMPLE 3

The following solution containing 200 mg/ml doxycycline activity was prepared using the procedure described in Example 1.

| | gm/100 ml |
|---|---|
| Doxycycline (based on a potency of 930 γ/mg plus a 5% overage) | 22.58 |
| Magnesium oxide | 3.828 |
| 2-Pyrrolidone | 50.00 |
| Sodium formaldehyde sulfoxylate | 1.00 |
| Concentrated hydrochloric acid, adjust to pH 7.2 | |
| Water q.s. to | 100 ml |

A solution comparable to the above was also made by adjusting the pH to 5.2.

EXAMPLE 4

The following solution containing 200 mg/ml of doxycycline activity was prepared using the procedure described in Example 1.

| | gm/100 ml |
|---|---|
| Doxycycline (based on a potency of 930 γ/mg plus a 5% overage) | 22.58 |
| Magnesium oxide | 3.828 |
| 2-Pyrrolidone | 40.00 |
| Sodium formaldehyde sulfoxylate | 1.00 |
| Concentrated hydrochloric acid, adjust to pH 7.0 | |
| Water q.s. to | 100 ml |

EXAMPLE 5

The following solution containing 200 mg/ml of doxycycline activity was prepared using the prodecure described in Example 1.

| | gm/100 ml |
|---|---|
| Doxycycline (based on a potency of 930 γ/mg plus a 5% overage) | 22.58 |
| Magnesium oxide | 3.828 |
| 2-Pyrrolidone | 30.00 |
| Sodium formaldehyde sulfoxylate | 1.00 |
| Concentrated hydrochloric acid, adjust to pH 5.8 | |
| Water q.s. to | 100 ml |

EXAMPLE 6

The following solution containing 200 mg/ml of doxycycline activity was prepared.

| | gm/100 ml |
|---|---|
| Doxycycline (based on a potency of 930 γ/mg plus a 5% overage) | 22.58 |
| Magnesium oxide | 3.828 |
| 2-Pyrrolidone | 40.00 |
| Sodium formaldehyde sulfoxylate | 1.00 |
| Polyvinylpyrrolidone K-17 | 5.00 |
| Concentrated hydrochloric acid, adjust to pH 6.6 | |

-continued

| | gm/100 ml |
|---|---|
| Water q.s. to | 100 ml |

The 2-pyrrolidone was mixed with water. Polyvinylpyrrolidone was then added and stirred until dissolved. The procedure as described in Example 1 was then followed.

A comparable solution was prepared using 30 gm of 2-pyrrolidone instead of 40 gm.

EXAMPLE 7

The following solution containing 100 mg/ml of doxycycline activity was prepared using the procedure described in Example 1.

| | gm/100 ml |
|---|---|
| Doxycycline hydrochloride (based on a potency of 850 γ/mg plus a 5% overage) | 12.353 |
| Magnesium oxide | 2.02 |
| 2-Pyrrolidone | 60.00 |
| Sodium formaldehyde sulfoxylate | 1.00 |
| Concentrated hydrochloride acid, to adjust pH to 7.2 | |
| Water q.s. to | 100 ml |

Solutions comparable to the above were also made by adjusting the pH to 6.5 and 5.0 respectively.

EXAMPLE 8

The following solution containing 100 mg/ml of doxycycline activity was prepared using the procedure described in Example 1.

| | gm/100 ml |
|---|---|
| Doxycycline (based on a potency of 930 γ/mg. plus a 5% overage) | 11.29 |
| Magnesium oxide | 0.059 |
| Sodium formaldehyde sulfoxylate | 1.00 |
| 2-Pyrrolidone | 70.00 |
| Concentrated hydrochloric acid, to adjust pH to 7.2 | |
| Water q.s. to | 100 ml |

Solutions comparable to the above were also made by adjusting the pH to 6.5 and 5.2 respectively.

EXAMPLE 9

The following solution containing 10 mg/ml of doxycycline activity was prepared using the procedure described in Example 1.

| | gm/100 ml |
|---|---|
| Doxycycline (based on a potency of 930 γ/mg plus a 5% overage) | 1.129 |
| Magnesium oxide | 0.206 |
| 2-Pyrrolidone | 10.00 |
| Sodium formaldehyde sulfoxylate | 1.00 |
| Concentrated hydrochloric acid, to adjust pH to 6.7 | |
| Water q.s. to | 100 ml |

A solution comparable to the above was also made by adjusting the pH to 5.

What is claimed is:

1. A doxycycline composition comprising an aqueous solution of from about 1 to 25% by weight of an antibiotic compound selected from the group consisting of doxycycline and the pharmaceutically acceptable acid addition salts thereof, from about 1.8 to 2.2 molar proportions based on said antibiotic of a pharmaceutically acceptable magnesium compound soluble in said solution, and from about 10 to 70% by weight of 2-pyrrolidone, said composition having a pH value in the range of from about 3 to 7.5.

2. A composition as claimed in claim 1 wherein said antibiotic compound is doxycycline.

3. A composition as claimed in claim 1 wherein said magnesium compound is introduced in the form of magnesium oxide.

4. A composition of claim 1 wherein polyvinylpyrrolidone having an average molecular weight of between 5,000 and 100,000 is also present in a concentration of from about 1 to 7% by weight of the total.

5. A composition as claimed in claim 1 wherein said antibiotic compound is present at the level of from about 5 to 20% by weight.

6. A composition as claimed in claim 1 wherein said antibiotic compound is present at a level of from about 10 to 20% by weight.

7. A composition as claimed in claim 1 having a pH value of from about 5 to 7.

8. A doxycycline composition comprising an aqueous solution of from about 10 to 20% by weight of doxycycline, from about 1.8 to 2.2 molar proportions based on doxycycline of a pharmaceutically acceptable magnesium compound soluble in said solution, from about 30 to 50% by weight of 2-pyrrolidone and from about 1 to 7% by weight of polyvinylpyrrolidone, said composition having a pH value in the range of from about 5 to 7.

* * * * *